United States Patent [19]
Vaillancourt

[11] Patent Number: 5,330,435
[45] Date of Patent: Jul. 19, 1994

[54] VALVE FOR A CATHETER ASSEMBLY
[76] Inventor: Vincent L. Vaillancourt, 14 Bunyan Dr., Livingston, N.J. 07039
[21] Appl. No.: 44,134
[22] Filed: Apr. 8, 1993
[51] Int. Cl.⁵ ............................................. A61M 5/178
[52] U.S. Cl. .................................. 604/167; 604/256; 604/283; 241/149
[58] Field of Search ............... 604/167, 164, 169, 256, 604/264, 283; 241/149.1, 149.3, 149.6, 149.8

[56]  References Cited
U.S. PATENT DOCUMENTS

| | | | |
|---|---|---|---|
| 4,512,766 | 4/1985 | Vailancourt | 604/256 |
| 4,610,469 | 9/1986 | Wolff-Mooij | 251/149.1 |
| 4,874,377 | 10/1989 | Newgard et al. | 604/167 |
| 5,053,014 | 10/1991 | Van Heugten | 604/167 |
| 5,064,416 | 11/1991 | Newgard et al. | 604/256 |
| 5,088,984 | 2/1992 | Fields | 604/167 |
| 5,211,634 | 5/1993 | Vaillancourt | 604/167 |

*Primary Examiner*—John G. Weiss
*Attorney, Agent, or Firm*—Francis C. Hand

[57]  ABSTRACT

The valve for a catheter includes an elasotmeric sheath for mounting over the end of the tube within a catheter assembly to prevent a backflow of blood. The valve also includes a sleeve of rubber or plastic which fits over the end of the sheath and which is resiliently expanded when the sheath is mounted on the tube so as to impart a circumferentially applied compressive force on the closed end of the sheath. The sleeve serves to maintain the wall in a sealed condition after a needle has been pierced through the wall and is subsequently removed.

15 Claims, 1 Drawing Sheet

VALVE FOR A CATHETER ASSEMBLY

This invention relates to a valve for a catheter assembly. More particular, this invention relates to a valve for an intravenous catheter assembly.

Heretofore, various types of catheters and catheter assemblies have been known for insertion in a vein of a patient. One of the most popular intravenous (IV) catheters in use is known as the over-the-needle catheter. In this case, the catheter is constructed of a hub from which a catheter needle extends. This catheter is constructed so as to receive a needle assembly having a needle which passes into and through the catheter needle. In use, the needle of the needle assembly is first inserted into the vein of a patient and, thereafter, the catheter is pushed over this needle into the vein. At the same time, in some cases, the needle of the needle assembly is simultaneously removed from the vein so as to leave the catheter needle in place.

Generally, such a catheter assembly has required the connection of a pre-primed IV administration set to the catheter hub in order to preclude a back flow of blood from the vein of the patient through the hub to the surrounding environment. Consequently, one of the major disadvantages of such a catheter is the requirement for manipulation of the administration set and/or manual dexterity in utilizing the catheter assembly.

Another disadvantage of the catheter assembly of the above type is that a significant percentage of the incidence of sepsis may be directly attributable to the manipulation of the administration set with the catheter assembly during a venipuncture procedure. Still another disadvantage is that there may be an escape of blood into the surrounding environment.

It has also been known from pending U.S. patent application Ser. No. 07/965,339, filed Oct. 23, 1992 that a catheter assembly can be constructed to have a tube located within a hub coaxial with a catheter while an elastomeric valve is mounted on an end of the tube remote from the catheter in order to seal the end of the tube against a flow of blood from the catheter. As described, the valve may be constructed of a pair of sheaths which are disposed over the tube in overlying relation. In this construction, each sheath has a closed end and the ends are spaced apart to define a gap or chamber. Such a valve permits the passage of a needle through the walls of the tube sheaths in order to perform a desired function. Upon withdrawal of the needle, the two sheaths re-seal. The use of the two sheaths in series eliminates leakage, particularly because of the reduced pressure which is developed from one sheath to the other.

It is an object of this invention to provide a simplified valve for sealing the end of a tube in a catheter assembly.

It is another object of the invention to be able to perform a bloodless venipuncture using a catheter assembly.

It is another object of the invention to provide a simplified IV catheter assembly in which blood is contained within a catheter after puncture of a vein in a venipuncture procedure.

It is another object of the invention to be able to hook up a conventional male luer fitting to a catheter hub and obtain fluid flow without undue pressure drop.

It is another object of the invention to be able to hook up a syringe directly to a catheter hub to obtain a blood sample without having to use a needle.

Briefly, the invention provides a valve assembly for sealing one end of a tube within a catheter assembly. In this respect, the valve includes an elastomeric sheath for sliding over one end of a tube with the sheath having a closed end defining a wall to seal the end of the tube against a flow of blood from the tube and an elastomeric sleeve which is concentrically mounted on the sheath. The sheath and sleeve are sized so that when the valve is mounted on a tube, the sleeve becomes radially stretched and applies a circumferentially applied compressive force on the wall of the sheath.

In one embodiment, the valve can be employed in a catheter which is constructed of a hub having a catheter secured to and extending from the hub to define a flow path. In addition, a tube is secured to and within the hub coaxially with the catheter in order to define a continuation of the flow path through the catheter. In accordance with the invention, the valve is mounted on the end of the tube which is remote from the catheter and which is disposed within the hub. As above, the sheath of the valve is disposed over the tube in overlying relation and has a closed end defining a wall to seal the end of the tube against a flow of blood from the catheter. The sleeve for imposing a circumferentially applied compressive force on the wall of the sheath is positioned to be outside the plane of the tube. That is, the sleeve is disposed in a plane longitudinally adjacent a plane of the tube. However, it is possible to have the plane of the sleeve project partially over the end of the tube provided the remainder of the sleeve imposes a sufficient compressive force on the wall of the sheath to maintain the wall in a sealed condition.

The catheter is particularly useful with a needle assembly, for example, employing a syringe having a needle extending therefrom. In this case, the needle of the needle assembly can be pierced through the wall of the sheath and slid through the tube and catheter so as to obtain a blood sample. In this embodiment, the needle of the needle assembly can also be sized so as to project into the vein of a patient if such is desired.

During use, when the closed end of the elastomeric sheath of the valve is pierced by a needle, an opening is caused in the sheath which remains until the needle is removed. When the needle is subsequently removed, there is a natural "recovery" of the material of the sheath, for example, being made of rubber, such as a latex rubber. However, in practice, the recovery is never complete so that a hole would be left in the wall of the sheath. Generally, such a hole would be determined by the original size of the hole, i.e. needle size, and the recoverability of the rubber of the sheath. If, for example, recovery was 100%, there would be no remaining hole in the sheath. Such is generally not the case in practice. By placing the elastomeric sleeve, which may be made of rubber or plastic, about the sheath near the closed end that is punctured and under some tension, it has been found that when the needle is removed, the recovery of the material of the sheath at the hole is 100% and the hole not only closes but can withstand a substantial amount of internal pressure before opening.

The outer sleeve is sized to exert enough compressive force on the wall of the sheath so that when a needle is removed, the compressive force compensates for the unrecovered portion of the material of the sheath thereby closing the hole and allowing the sheath to withstand a surprising high pressure, for example, from 6 to 8 psi, before leaking.

The catheter assembly may also be used to permit passage of a wire or the like into the vein of a patient while maintaining a sealed condition.

In still another embodiment, the catheter assembly can be joined to a male luer connector. In this case, the male luer connector may have a bore to slidably receive the end of the tube disposed within the hub of the catheter assembly while the end wall of the sheath is provided with a slit. In use, the distal end of the male luer connector pushes the sheath and sleeve of the valve over the end of the tube and along the outside surface of the tube during the formation of a connection. During this time, the slit in the end wall of the sheath allows the wall to stretch open to slide over the end of the tube. In this embodiment, the tube within the hub of the catheter assembly serves as a connecting piece between the male luer connector and the catheter of the catheter assembly. Upon removal of the male luer connector from the hub of the catheter assembly, the natural resilience of the sheath of the valve causes the sheath to spring back over the exposed end of the tube so that the closed end of the sheath again serves as a wall to prevent a flow of blood from the tube of the catheter assembly. At this time, the sleeve re-exerts a circumferentially applied compressive force on the closed end of the sheath so as to maintain the wall in a sealed condition.

The catheter may be used in various manners, such as those described in copending application Ser. No. 07/965,339, filed Oct. 23, 1992 now U.S. Pat. No. 5,234,410.

The amount of compression imparted by the elastomeric sleeve on the elastomeric sheath may be relatively small so as to not interfere with the removal of a needle from the valve, for example, after a venipuncture is accomplished. For example, where the tube on which the valve is mounted has an outside diameter of 0.050 inch and the sheath has a thickness of 0.030 inch, the sleeve may have a longitudinal length of 0.050 inch, an inside diameter of 0.100 inch and an outside diameter of 0.140 inch. Thus, the inside diameter of the sleeve, when relaxed, is slightly larger than the outside diameter of the sheath, for example, by 0.010 inch. Accordingly, the force required to push the catheter assembly from a needle can remain very low thereby preserving a major attribute of the existing over-the-needle venipuncture insertion technique.

Likewise, where the sheath and sleeve are both slid over the closed tube in the embodiment using a male luer connector, the amount of compression imparted by the sleeve on the sheath and tube is not sufficient to prevent the spring back of the sheath after the male luer connector has been removed.

These and other objects and advantages of the invention will become more apparent from the following detailed description taken in conjunction with the accompanying drawings wherein.

Figure 1:
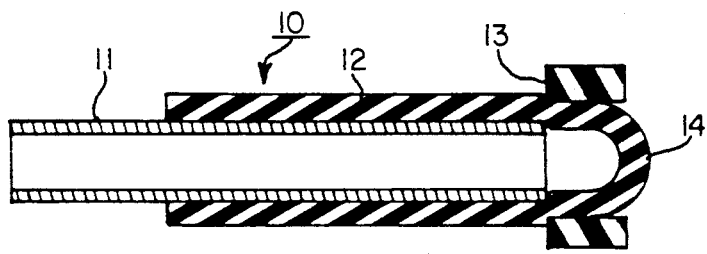
FIG. 1 illustrates a cross-sectional view of a valve constructed in accordance with the invention.

Referring to FIG. 1, the valve assembly 10 is constructed to fit on a tube 11, for example, which may be of circular cross-section and which may have a tapered end.

The valve 10 is formed of a sheath 12 and a sleeve 13. The sheath 12 may be made of rubber, such as a latex rubber, or any other suitable elastomeric material. As indicated, the sheath 12 has a closed end which defines a wall 14 spaced from the end of the tube 11. The sheath 12 is made of relatively thin material, for example, in the range of from 0.010 inch to 0.040 inch. In the illustrated embodiment, for a tube 11 having an outside diameter of 0.050 inches, the sheath 12 may have a wall thickness of 0.030 inches.

The sleeve 13 of the valve 10 may be made of any suitable elastomeric material such as a rubber or plastic. As illustrated, the sleeve 13 is mounted over the sheath 12 and is of circular ring shape. When the valve 10 is disposed over the tube 11 the sleeve 13 is brought into a position such that the plane of the sleeve 13 is longitudinally adjacent to the plane of the end of the sleeve 11. That is to say, the sleeve 13 does not overlap the end of the tube 11. Alternatively, the sleeve 13 may project into the plane of the tube 11 provided the "pinching" action of the sleeve 13 on the closed end of the sheath 12 is not impaired.

When the valve 10 is mounted on the tube 11, the sleeve 13 is radially expanded or stretched to a slight degree sufficient to impose a circumferentially applied compressive force on the wall 14 of the sheath 12. For example, where the sheath has a thickness of 0.030 inches, the sleeve has a longitudinal length of 0.050 inches and an inner diameter of 0.100 inch and an outer diameter of 0.140 inch.

Figure 2:
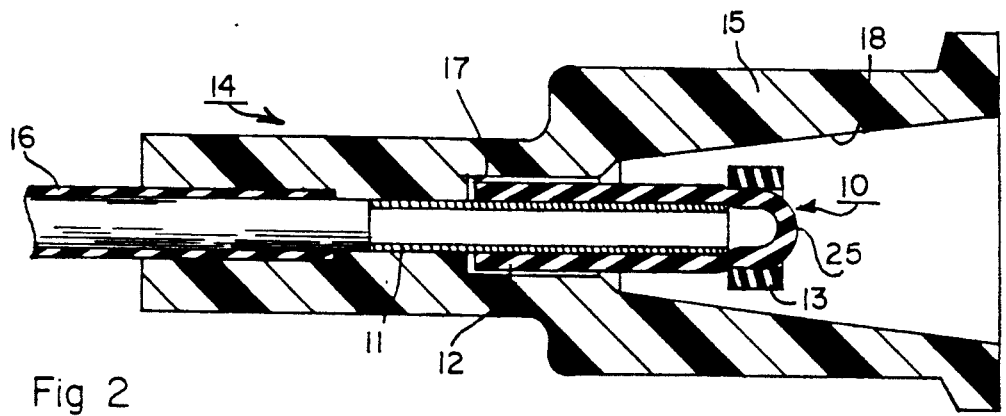
FIG. 2 illustrates a cross-sectional view of a catheter assembly employing the valve of FIG. 1 in accordance with the invention.

Referring to FIG. 2, wherein like reference characters indicate like parts as above, the valve 10 is employed in a catheter assembly 14 which includes a hub 15 of conventional structure and a catheter 16 which is secured to and which extends from the hub 15 to define a flow path, for example, for blood. As shown, the tube 11 is disposed in the hub 15 coaxially of the catheter 16. In addition, the sheath 12 projects into a recess 17 within the hub 15.

As illustrated, the hub 15 may be made of a plastic material and includes a conically shaped luer 18. In addition, the valve 10 is disposed within the luer 18 of the hub 15 in a recessed condition.

The tube 11 may be in the form of a stainless steel needle which is sealed within the hub 15, for example, using adhesive, an interference fit or other suitable connection means. In addition, the tube 11 extends into the bore 18 of the hub 15 to terminate at a point spaced within the hub 15.

Figure 3:
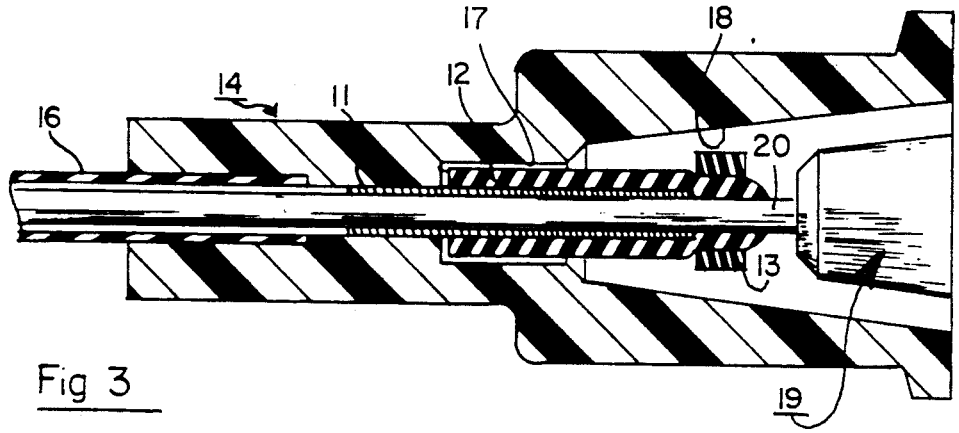
FIG. 3 illustrates a cross-sectional view of a catheter assembly connected with a needle assembly in accordance with the invention.

Referring to FIG. 3, wherein like reference characters indicate like parts as above, the catheter assembly 14 may be used in combination with a needle assembly 19, for example, in order to carry out a venipuncture. In this respect, the needle assembly 19 has a needle 20 which is mounted in and which projects from a clear plastic needle holder 21. This needle 20 is sized so as to be disposed coaxially within the tube 11 and the catheter 16 of the catheter assembly 14 while being of a length to extend from the catheter 16 into a vein of a patient (not shown). In addition, the needle 20 has a sharp end for piercing through the wall 14 of the sheath 12 of the valve 10 in seal-tight relation. As illustrated, the wall 14 seals over the needle 20 (when the needle 20 is pierced through the wall 14). At the same time, the elastomeric sleeve 13 expands slightly and enhances the sealing fit between the wall 14 and the needle 20.

As indicated in FIG. 3, the needle holder 21 may be sized and shaped to be disposed within the bore 18 of the hub 15 of the catheter assembly 14 when the needle 20 of the needle assembly 19 has been inserted into a vein.

In use, the needle 20 of the needle assembly 19 can be passed through the skin of the patient into a vein, such as a peripheral vein, using a known technique. Upon venipuncture, blood will flow through lumen of the needle 20 and into the clear plastic needle holder 21, at which time, blood (flashback) will be seen. This is an indication to the practitioner that the vein has been penetrated and that the procedure may advance to the next stage. Thereafter, the catheter assembly 14 can be pushed over the needle 20 for passage of the catheter 16 into the vein. At the same time, or shortly thereafter, the needle assembly 20 is withdrawn from the vein as well as from the catheter 14. At this time, the sheath 12 of the valve 10 returns to the position as shown in FIG. 2. That is, withdrawal of the needle 19 allows the wall 14 to collapse about the opening caused by the needle 20. In addition, the sleeve 13 imposes a circumferentially applied compressive force on the wall to ensure closing of the opening caused by the needle 20. The catheter assembly 14 may be left in this condition without concern for blood leakage. In this respect, it has been found that the valve 10 is able to withstand pressures of from 6 to 8 psi before leaking blood therefrom.

Figure 4:
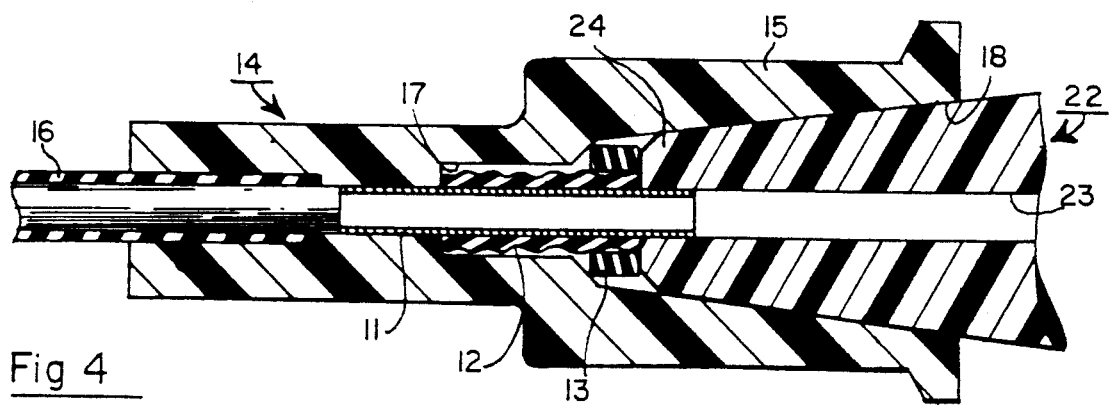
FIG. 4 illustrates a cross-sectional view of a connection between a male luer connector and a catheter assembly of FIG. 2 in accordance with the invention.

Referring to FIG. 4, wherein like reference characters indicate like parts as above, the catheter assembly 14 may also be used in combination with a male luer connector 22. As indicated, the connector 22 has a longitudinal bore 23 which is sized to slidably receive one end of the tube 11 of the catheter assembly 14 in seal-tight relation. In addition, a forward end 24 of the connector 22 is matingly received in the bore 18 of the hub 15. As indicated, the forward end 24 of the connector 22 serves to push the sheath 12 and sleeve 13 over the end of the tube 11 so that the sheath 12 becomes compressed between the forward end 24 of the connector 22 and an interior of the hub 15. In this respect, the wall 14 of this sheath 12 is provided with a slit 25 (FIG. 2) to permit the wall 14 to expand about the slit 25 and thus stretch over the end of the tube 11 when the connector 22 is pushed into the hub 15. Upon removal of the connector 22 from the hub 15, the sheath 12 springs back into the position as shown in FIG. 2, again sealing over the end of the tube 11 in a manner as described above.

The action of the male luer connector 23 in pushing the sheath 12 of the valve 10 over the tube 11 accomplishes two objectives. First, the connector 23 may now be secured in a normal manner to the hub 15 and, secondly, the lumen to the catheter 16 is opened allowing for fluid communication between the vein of a patient and a connected administration set (not shown) which is connected with the male luer connector 22. There is no need for a needle to pierce the sheath 12 to obtain a blood sample.

Of note, in the embodiment illustrated in FIG. 4, a spring means may be provided to assist the return of the compressed sheath 12 over the tube 11 upon removal of the male luer connector 22.

The invention thus provides a valve for a catheter assembly which is of relatively simple construction and which is able to prevent blood backflow and leakage upon removal of a needle assembly or male luer connector from catheter assembly.

The valve is self-sealing and provides a reliable seal against leakage of blood. Further, the valve may be used more than once so that replacement is not required after one use.

What is claimed is:

1. A catheter comprising
   a hub;
   a catheter secured to and extending from said hub to define a flow path;
   a tube secured to and within said hub to define a flow path, said tube being coaxial with said catheter; and
   an elastomeric valve mounted on one end of said tube remote from said catheter and within said hub, said valve having a sheath disposed over said tube in overlying relation and having a closed end defining a wall to seal said one end of said tube against a flow of blood from said catheter and a sleeve concentrically mounted on said sheath, said sleeve begin, radially stretched on said sheath to maintain a circumferentially applied compressive force on said wall of said sheath.

2. A catheter as set forth in claim 1 wherein said sheath is made of rubber and said sleeve is made of a material selected from the group consisting of rubber and plastic.

3. A catheter as set forth in claim 1 wherein said wall has a thickness in the range of from 0.010 inch to 0.040 inch.

4. A catheter as set forth in claim 1 wherein said hub has a conically shaped bore for receiving a tapered male luer hub therein in mating relation.

5. A catheter as set forth in claim 1 wherein said sleeve is in a plane longitudinally adjacent a plane of said tube.

6. A catheter as set forth in claim 1 wherein said tube has an outside diameter of 0.050 inches, said sheath has a wall thickness of 0.030 inches and said sleeve has a longitudinal length of 0.050 inches.

7. In combination
   a catheter assembly having a hub and a catheter secured to and extending from said hub to define a flow path, a tube secured to and within said hub coaxially of said catheter, and an elastomeric valve on one end of said tube, said valve having a wall disposed transversely of said tube to seal said one end of said tube against a flow of blood from said catheter and a sleeve disposed about said wall to maintain a circumferentially applied compressive force on said wall; and
   a needle assembly having a needle piercing said wall and disposed coaxially within said tube and said catheter, said needle being disposed to extend into said catheter.

8. A catheter assembly as set forth in claim 7 wherein said needle assembly includes a holder mounting said needle therein and being disposed in said hub.

9. A catheter assembly as set forth in claim 8 herein said hub has a conically shaped bore and said holder is matingly received in said bore.

10. A catheter assembly as set forth in claim 8 wherein said sheath is made of rubber and said sleeve is made of one of rubber and plastic.

11. In combination, a catheter assembly having a hub, a catheter secured to and extending from said hub to define a flow path and a tube secured to and within said hub coaxially of said catheter;

a male luer connector having a longitudinal bore slidably receiving one end of said tube therein in seal-tight relation and a forward end matingly received in said hub;

an elastomeric sheath mounted on said one end of said tube and being compressed between said forward end of said male luer connector and an interior of said hub, said sheath being expandable into a position sealing over said one end of said tube upon removal of said male luer connector from said catheter to seal said tube end against a flow of blood from said catheter; and a sleeve concentrically mounted on said sheath, said sleeve being radially stretched on said sheath in said position to maintain a circumferentially applied compressive force on said sheath to seal said tube end against a flow of blood from said catheter.

12. The combination as set forth in claim 11 wherein said sheath is made of rubber and said sleeve is made of one of rubber and plastic.

13. The combination as set forth in claim 11 wherein said tube has an outside diameter of 0.050 inches, said sheath has a wall thickness of 0.030 inches and said sleeve has a longitudinal length of 0.050 inches.

14. A valve for sealing one end of a tube, said valve comprising, an elastomeric sheath for sliding over one end of the tube, said sheath having a closed end defining a wall to seal the end of the tube against a flow of blood from the tube and to permit penetration of a needle therethrough; and an elastomeric sleeve concentrically mounted on said sheath, said sleeve being radially stretched with said sheath being mounted on the tube to apply a circumferential compressive force on said wall of said sheath to maintain said wall in a sealed condition after removal of a needle therefrom.

15. A valve as set forth in claim 14 wherein said sheath has a thickness of 0.030 inches and an inside diameter of 0.050 inches and said sleeve has a longitudinal length of 0.050 inches and an outside diameter of 0.100 inches.

* * * * *